United States Patent

Beijert

(10) Patent No.: US 9,417,308 B2
(45) Date of Patent: Aug. 16, 2016

(54) APPARATUS AND METHOD FOR INSPECTING PINS ON A PROBE CARD

(71) Applicant: Stichting Continuiteit Beijert Engineering, Hattem (NL)

(72) Inventor: Oscar Beijert, Elspeet (NL)

(73) Assignee: Stichting Continuiteit Beijert Engineering, Hattem (NL)

( * ) Notice: Subject to any disclaimer, the term of this patent is extended or adjusted under 35 U.S.C. 154(b) by 0 days.

(21) Appl. No.: 14/323,784

(22) Filed: Jul. 3, 2014

(65) Prior Publication Data

US 2015/0010205 A1 Jan. 8, 2015

Related U.S. Application Data

(60) Provisional application No. 61/842,940, filed on Jul. 3, 2013.

(51) Int. Cl.
| | |
|---|---|
| *G06K 9/00* | (2006.01) |
| *G01R 35/00* | (2006.01) |
| *G01N 21/95* | (2006.01) |
| *G01B 11/02* | (2006.01) |

(52) U.S. Cl.
CPC ............. *G01R 35/00* (2013.01); *G01B 11/022* (2013.01); *G01N 21/95* (2013.01); *G01N 2201/10* (2013.01)

(58) Field of Classification Search
USPC .......................................... 382/103; 356/244
See application file for complete search history.

(56) References Cited

U.S. PATENT DOCUMENTS

| | | | |
|---|---|---|---|
| 4,918,374 A | 4/1990 | Stewart et al. | |
| 5,471,148 A * | 11/1995 | Sinsheimer ........ | G01R 1/07314 |
| | | | 324/750.25 |
| 5,831,443 A | 11/1998 | Quarre et al. | |
| 6,002,426 A | 12/1999 | Back et al. | |
| 6,118,894 A | 9/2000 | Schwartz et al. | |
| 6,239,590 B1 | 5/2001 | Krivy et al. | |
| 6,501,289 B1 | 12/2002 | Takekoshi | |
| 6,986,211 B2 | 1/2006 | Gunderson | |
| 6,992,500 B2 | 1/2006 | Sugiyama et al. | |

(Continued)

FOREIGN PATENT DOCUMENTS

| | | |
|---|---|---|
| CN | 1546287 A | 11/2004 |
| JP | 5-157790 A | 6/1993 |

(Continued)

OTHER PUBLICATIONS

PCT Notification of Transmittal of the International Search Report and the Written Opinion of the International Searching Authority for International Application No. PCT/IB2014/001264 dated Dec. 15, 2014; 14 total pages.

*Primary Examiner* — Yon Couso
(74) *Attorney, Agent, or Firm* — Patterson & Sheridan, LLP

(57) ABSTRACT

Embodiments described herein generally relate to methods and apparatuses for ensuring the integrity of probe card assemblies and verifying that probe cards are ready for testing. In one embodiment, an apparatus includes a stage that allows stable and precise movement of a sensor. The stage includes a first support, a second support, and a sensor carrier. A plurality of lifting devices is coupled to the second support and the sensor carrier, providing a more stable and precise movement for the sensor carrier. Methods for identifying objects other than the probes disposed on a surface of a probe card and to determine whether the probe card is ready for use are disclosed.

11 Claims, 14 Drawing Sheets

(56) References Cited

U.S. PATENT DOCUMENTS

| | | | |
|---|---|---|---|
| 8,729,917 B2 * | 5/2014 | Gunderson | G01R 31/2891 324/750.19 |
| 2003/0173951 A1 | 9/2003 | Suzuki | |
| 2003/0223078 A1 | 12/2003 | Van Doren et al. | |
| 2005/0017708 A1 | 1/2005 | Miller et al. | |
| 2007/0132468 A1 | 6/2007 | Nakayama | |
| 2007/0257686 A1 | 11/2007 | Beijert | |
| 2007/0296427 A1 | 12/2007 | Kono | |
| 2008/0197865 A1 | 8/2008 | Endres | |
| 2010/0213960 A1 | 8/2010 | Mok et al. | |
| 2012/0150475 A1 | 6/2012 | Strom et al. | |
| 2014/0015955 A1 | 1/2014 | Beijert | |

FOREIGN PATENT DOCUMENTS

| | | |
|---|---|---|
| JP | 2003-172418 A | 6/2003 |
| JP | 2005-79253 A | 3/2005 |
| KR | 0180610 B1 | 4/1999 |
| KR | 2009-0068902 A | 6/2009 |
| KR | 2010-0041578 A | 4/2010 |

* cited by examiner

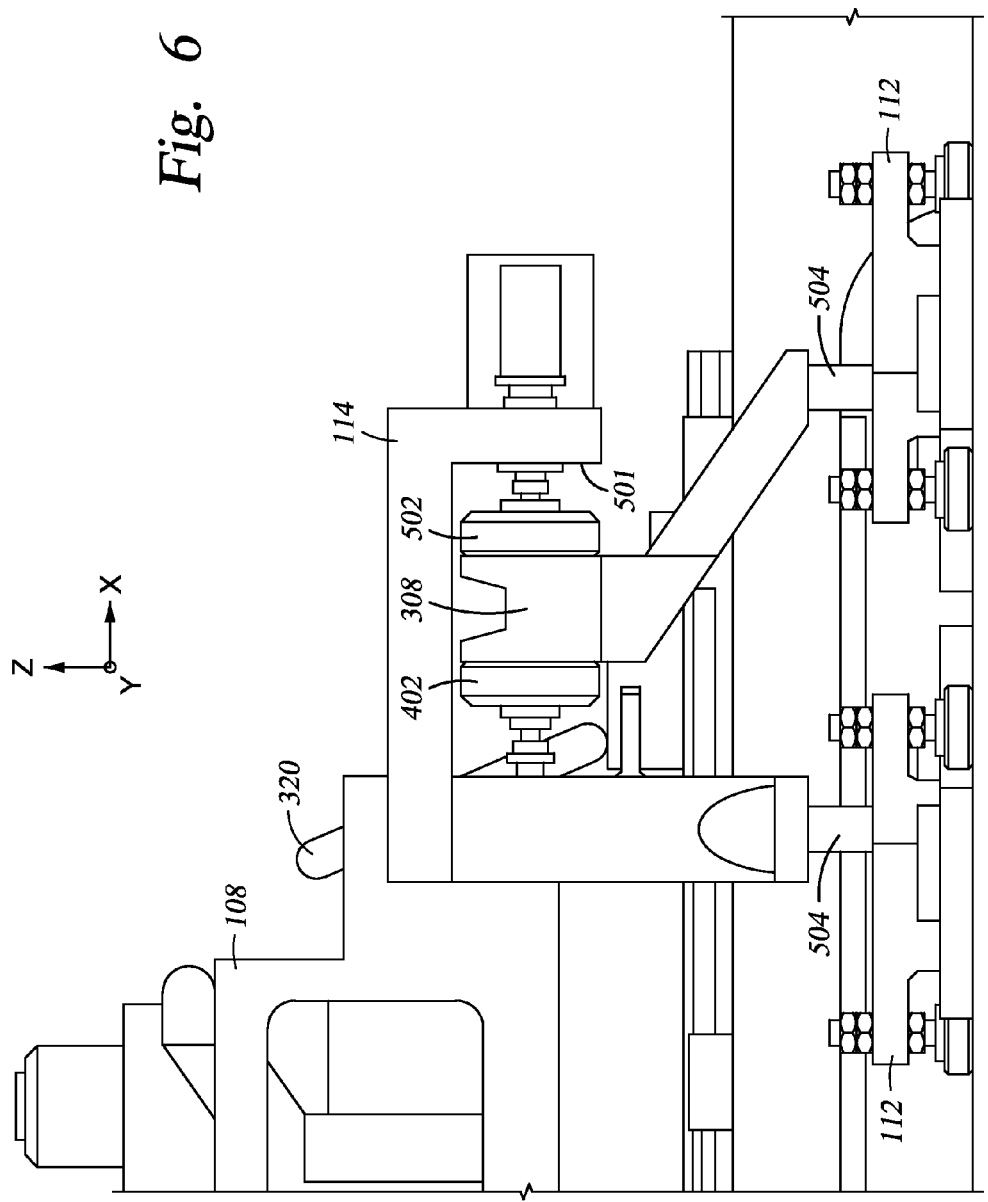

APPARATUS AND METHOD FOR INSPECTING PINS ON A PROBE CARD

CROSS-REFERENCE TO RELATED APPLICATIONS

This application claims the benefit of U.S. Provisional Patent Application Ser. No. 61/842,940 (BEIJ/0005USL), filed Jul. 3, 2013, which is incorporated herein by reference.

BACKGROUND

1. Field

Embodiments described herein generally relate to integrated circuit testing, and more particularly, to apparatuses and methods for testing probe cards used to test integrated circuits on a wafer.

2. Description of the Related Art

Probe card test and verification systems are commonly used as production tools for the characterization of probe cards (used in testing integrated circuit devices/substrates) before and after use and to facilitate rework of probe cards that do not conform to predefined standards. Such systems typically consist of a computer, a precision measurement system, a software based vision system, and precision motion control and measurement system. Such equipped systems allow for the measurement and adjustment of probe card planarization, visual X/Y location and adjustment, probe contact resistance, leakage and component measurements.

Electrical parameters including contact resistance and leakage may also be measured against reference values and an indication may be provided as to whether a probe card assembly under test has passed or failed. If a failure is determined, a full report may be printed to accompany the card for rework. Quick verification provided by such systems may validate that a probe card assembly is ready for test or is in need of rework.

Therefore, there is a continuing need to improve such systems to that ensure the integrity of probe card assemblies and verify that probe cards are ready for testing.

SUMMARY

Embodiments described herein generally relate to methods and apparatuses for ensuring the integrity of probe card assemblies and verifying that probe cards are ready for testing.

In one embodiment, an apparatus for analyzing a probe card is disclosed. The apparatus includes a stage. The stage includes a base, a first support, and a second support. The second support is coupled to a first plurality of lifting devices. The stage further includes a sensor carrier disposed over the first and second supports, and the sensor carrier is coupled to a second plurality of lifting devices. The stage further includes a sensor disposed on the sensor carrier.

In another embodiment, an apparatus for analyzing a probe card is disclosed. The apparatus includes an enclosure enclosing a stage. The stage includes a base, a first support, and a second support. The second support is coupled to a first plurality of lifting devices. The stage further includes a sensor carrier disposed over the first and second supports, and the sensor carrier is coupled to a second plurality of lifting devices. The stage further includes a sensor disposed on the sensor carrier. The apparatus further includes a controller and a display.

In another embodiment, a method is disclosed. The method includes scanning a surface of a probe card, obtaining a reference shape of an array of probes from a reference file, locating the array of probes on the surface based on the reference shape, and enhancing images of probes in the array of probes.

BRIEF DESCRIPTION OF THE DRAWINGS

So that the manner in which the above recited features of the disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 6 is an enlarged view of a portion of the sensor carrier and the second support according to embodiments described herein.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments described herein generally relate to methods and apparatuses for ensuring the integrity of probe card assemblies and verifying that probe cards are ready for testing. In one embodiment, an apparatus includes a stage that allows stable and precise movement of a sensor. Suitable apparatus, such as INSPECTOR, that may be used to practice the embodiments described herein may be obtained from Stichting Continuities Beijert Engineering, The Netherlands. It is to be understood that the embodiments discussed herein may be practiced on other apparatus, including those sold by other manufacturers. The apparatus may be used to process probe cards that are 200 mm in diameter, 300 mm in diameter, 450 mm in diameter and any diameter probe cards desired.

Figure 1:
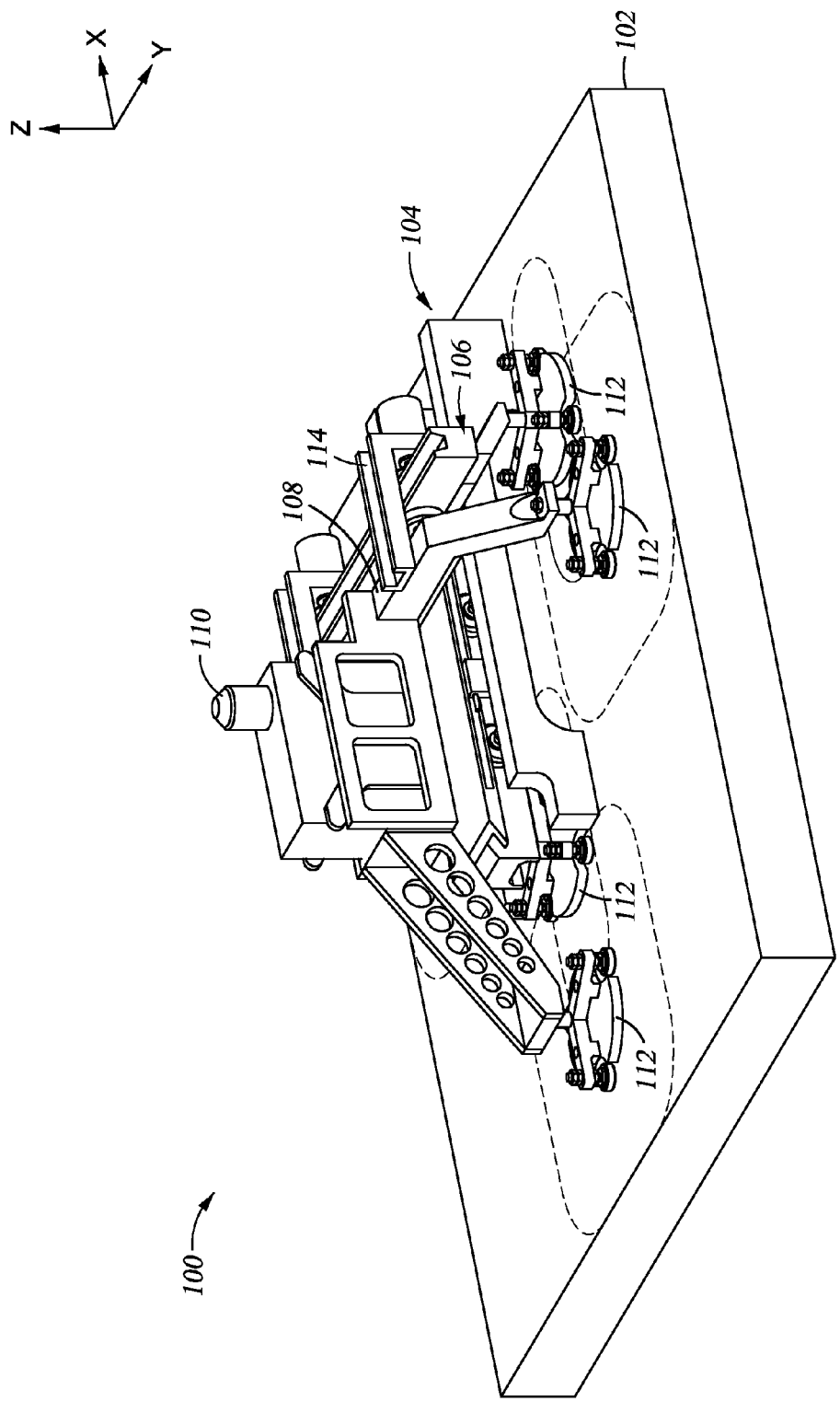
FIG. 1 is a perspective view of a stage according to embodiments described herein.

FIG. 1 is a perspective view of a stage 100 according to embodiments described herein. The stage 100 includes a base 102, a first support 104, a second support 106, and a sensor carrier 108 disposed over the first and second supports 104, 106. The base 102 may be made of granite stone. A sensor 110 is disposed on the sensor carrier 108, and the sensor 110 may be any imagine capturing sensor, such as a laser microscope, a stereo microscope, or any suitable sensor. The sensor carrier 108 and the second support 106 each includes a plurality of lifting devices 112. A bracket 114 is coupled to the sensor carrier 108 and a portion of the second support 106 is disposed between the sensor carrier 108 and the bracket 114. During operation, the lifting devices 112 lift the sensor carrier 108 and the second support 106 off the base 102 while the sensor carrier 108 and the second support 106 are moving in the X and/or Y directions, leading to a more stable and precise movement of the sensor 110.

Figure 2:
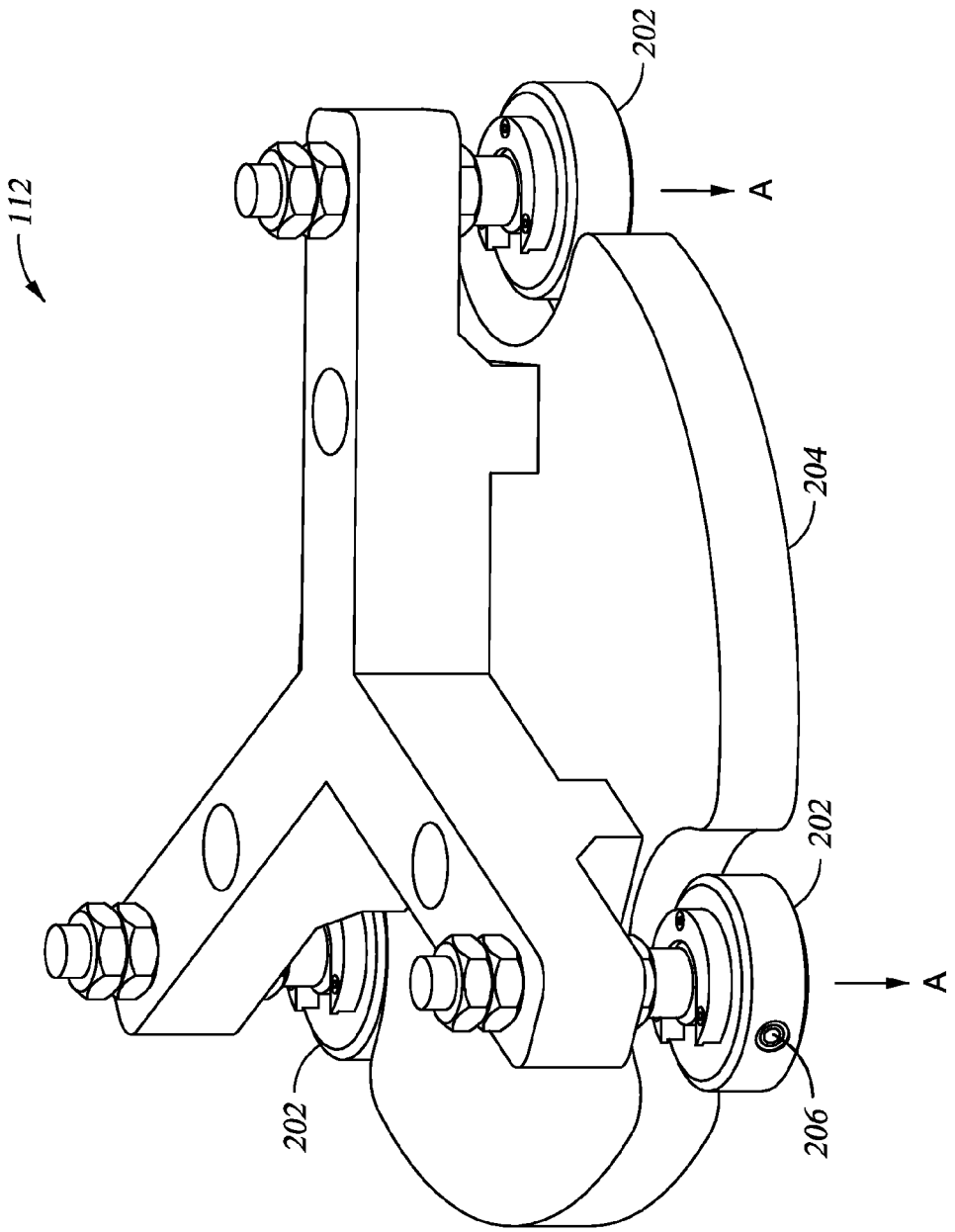
FIG. 2 is a perspective view of a lifting device according to embodiments described herein.

FIG. 2 is a perspective view of a lifting device 112 according to embodiments described herein. The lifting device 112 includes a plurality of air bearings 202 and a vacuum chuck 204. Each air bearing 202 has an inlet 206 supplying air to the air bearing 202, and the air is coming out from the bottom of the air bearing 202 indicated by the arrow "A," lifting the sensor carrier 108 and the second support 106 off the base 102. The number and locations of the air bearings 202 on a lifting device 112 may be specified to provide a more stable and precise lifting of the sensor 110. In one embodiment, there are three air bearings 202 on a lifting device 112, and the air bearings 202 are 120 degrees positioned, as shown in FIG. 2. In one embodiment, air having a pressure of 5.5 bar is introduced into each air bearing 202, and a total of 1000 N of lift force is generated in each lifting device 112. The vacuum cup 204 provides a smooth movement of the sensor 110 in the X and Y directions. During operation, the vacuum cup 204 pulls the air from the base 102, preventing the sensor carrier 108 and the second support 106 from jumping in the Z direction and keeping the sensor carrier 108 flat and stable when moving in the X and Y directions. With the vacuum cup 204, the sensor carrier 108 and the second support 106 may be lifted from the base 102 by the air bearings 202, and the distance between the lifting devices 112 and the base 102 ranges from about 2 microns to about 20 microns. Without the vacuum cup 204, the distance between the lifting devices 112 and the base 102 ranges from about 2 microns to about 100 microns. In one embodiment, the vacuum cup creates about 500 mBar of vacuum and about 1000 N of retraction force.

Figure 3A:
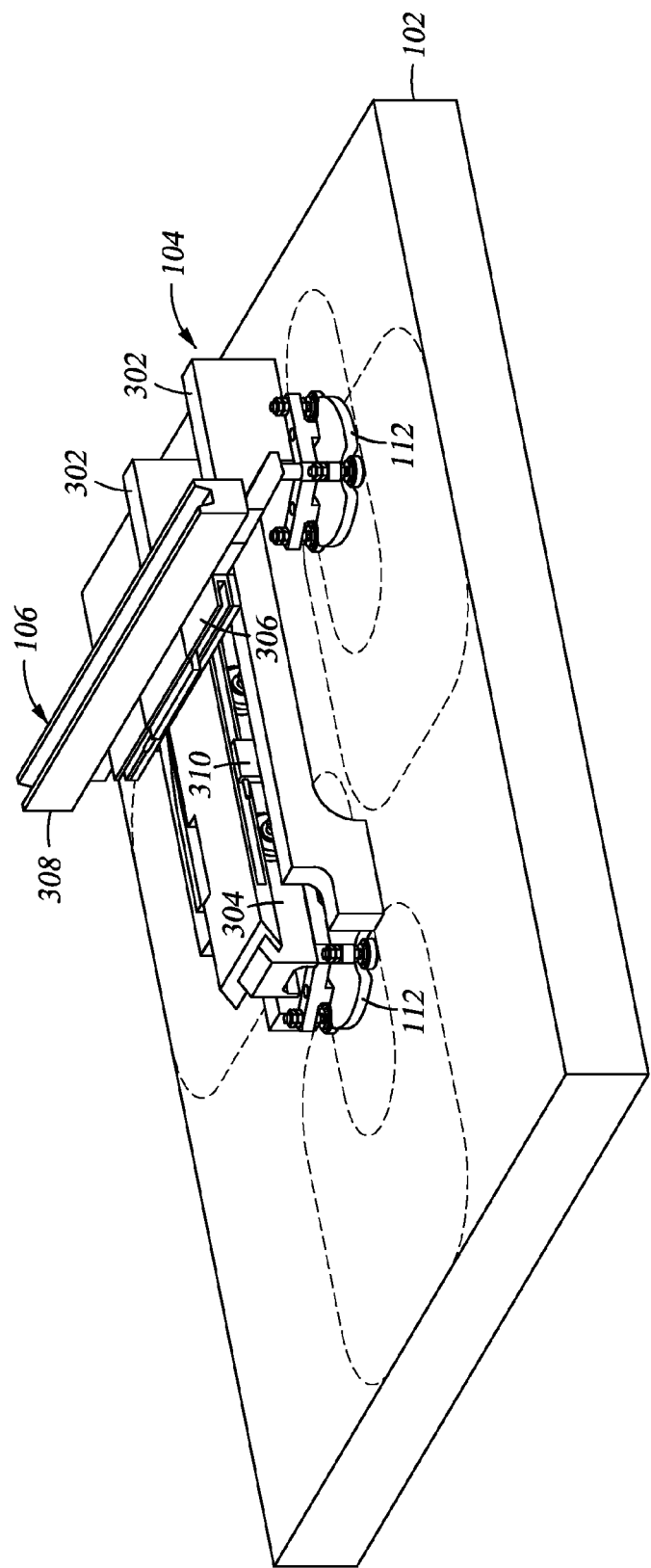
FIGS. 3A-3C illustrate a base, a first support and a second support of the stage according to embodiments described herein.

FIG. 3A is a perspective view of the base 102, the first support 104, and the second support 106 according to embodiments described herein. The first support 104 includes two parallel rails 302 that are fixed to the base 102. The second support 106 includes a first beam 304 disposed between the rails 302, a rotor 306 disposed on the beam 304, and a second beam 308 that is substantially perpendicular to the first beam 304. The rail 302 may function as a stator, and together with the rotor 306, the second support 106 is capable of moving in the X direction. The rail 302 and the rotor 306 may form a linear motor. An encoder 310 may be disposed on the first beam 304 of the second support 106 for controlling the position of the second support 106. Both the encoder 310 and the rotor 306 are connected to a driver (not shown), and the encoder 310 determines the position of the rotor 306 and feeds the information back to the driver. The encoder 310 is disposed at a location to have a short force loop that would provide minimum positioning error. The location of the encoder 310 provides more accurate controlling of the movement of the second beam 106. A plurality of lifting devices 112 are coupled to the second support 106. In one embodiment, a lifting device 112 is coupled to the first beam 304 and two lifting devices 112 are coupled to opposite ends of the second beam 306.

Figure 3B:
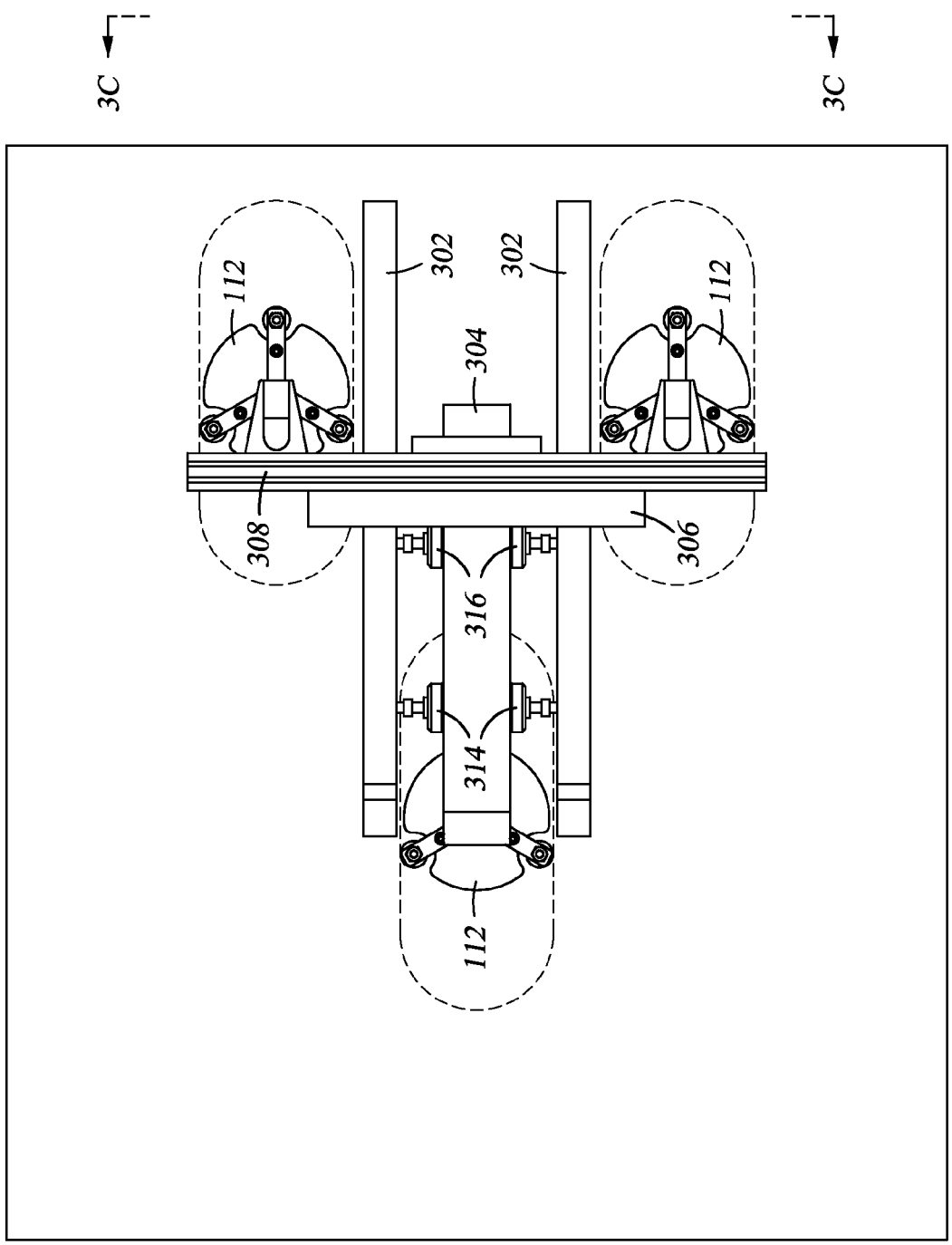
Figure 3C:
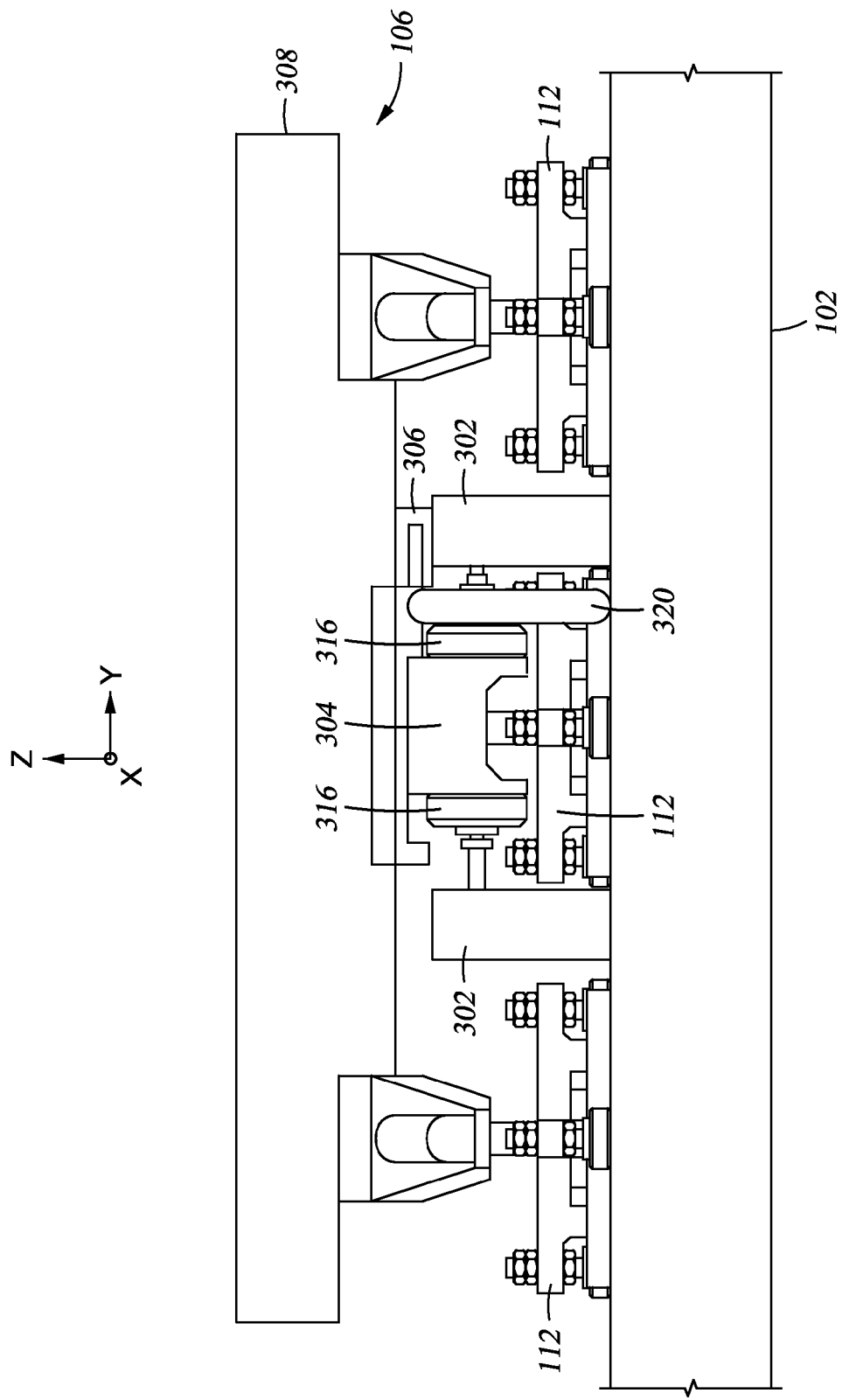
Figure 4:
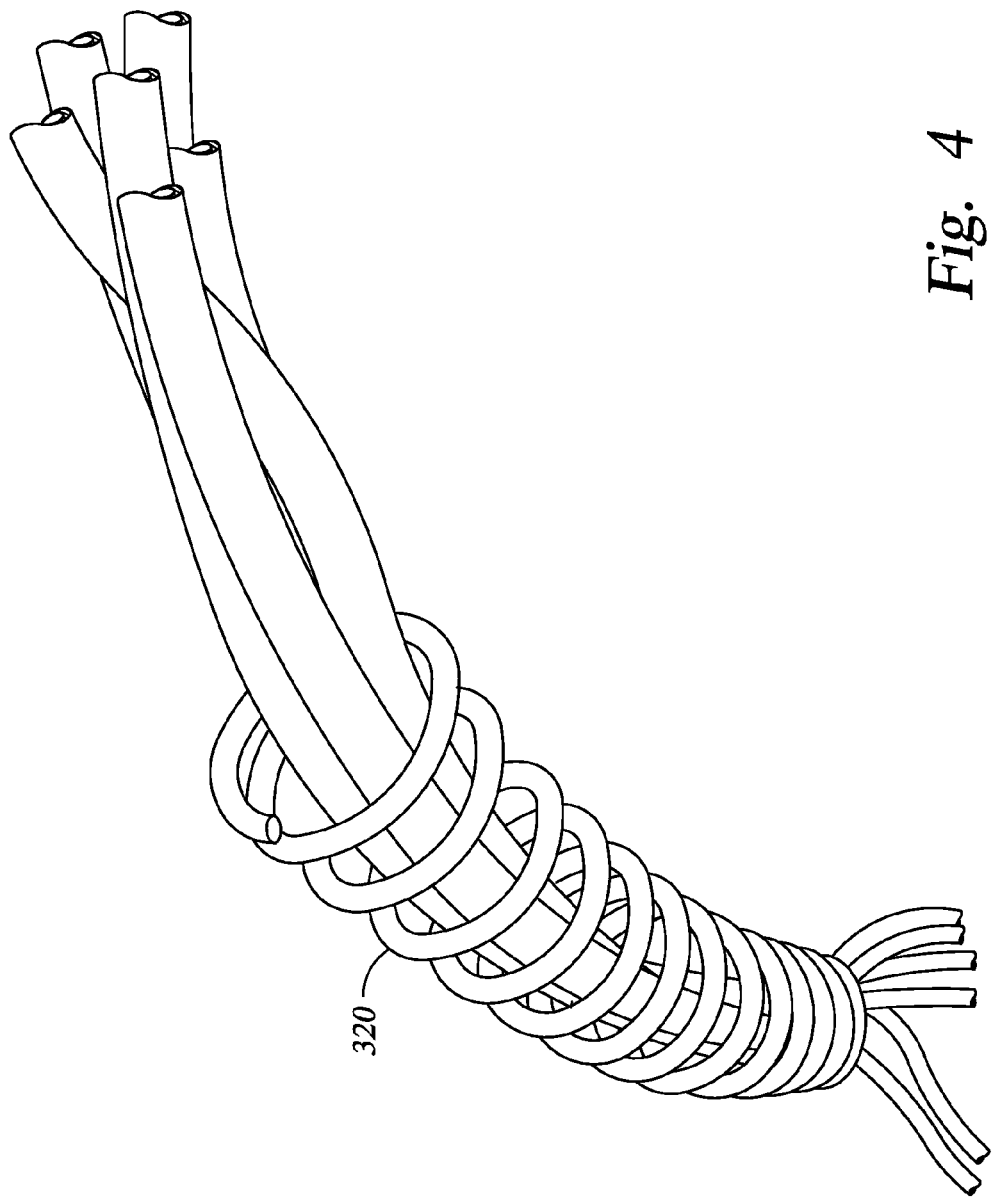
FIG. 4 illustrates a coil enclosing a plurality of cables according to embodiments described herein.

FIG. 3B is a top view of the base 102, the first support 104, and the second support 106 according to embodiments described herein. As shown in FIG. 3B, a first pair of air bearings 314 and a second pair of air bearings 316 are coupled to the rails 302, and the first beam 304 is place between the pairs of air bearings 314, 316. During operation, air is coming out of the pairs of the air bearings 314, 316 to stabilize the second support 106 as the second support 106 is moving in the X direction. FIG. 3C is a side view of the structure shown in FIG. 3B from line 3C. During operation, lifting devices 112 lift the second support 106 off the base 102, and the rotor 306 is lifted off the rails 302. The rotor 306 and the rail 302 acting as a stator causing the second support 106 to move in the X direction. Again the air coming out of the pairs of air bearings 314, 316 pushes on the first beam 304 to stabilize the second support 106 while the second support 106 is moving in the X direction. To protect the electrical cables used to provide power to the rotor 306 and encoder 310 from being damaged during operation, a coil 320 may be used to enclose the cables. FIG. 4 illustrates the coil 320 enclosing a plurality of cables.

Figure 5A:
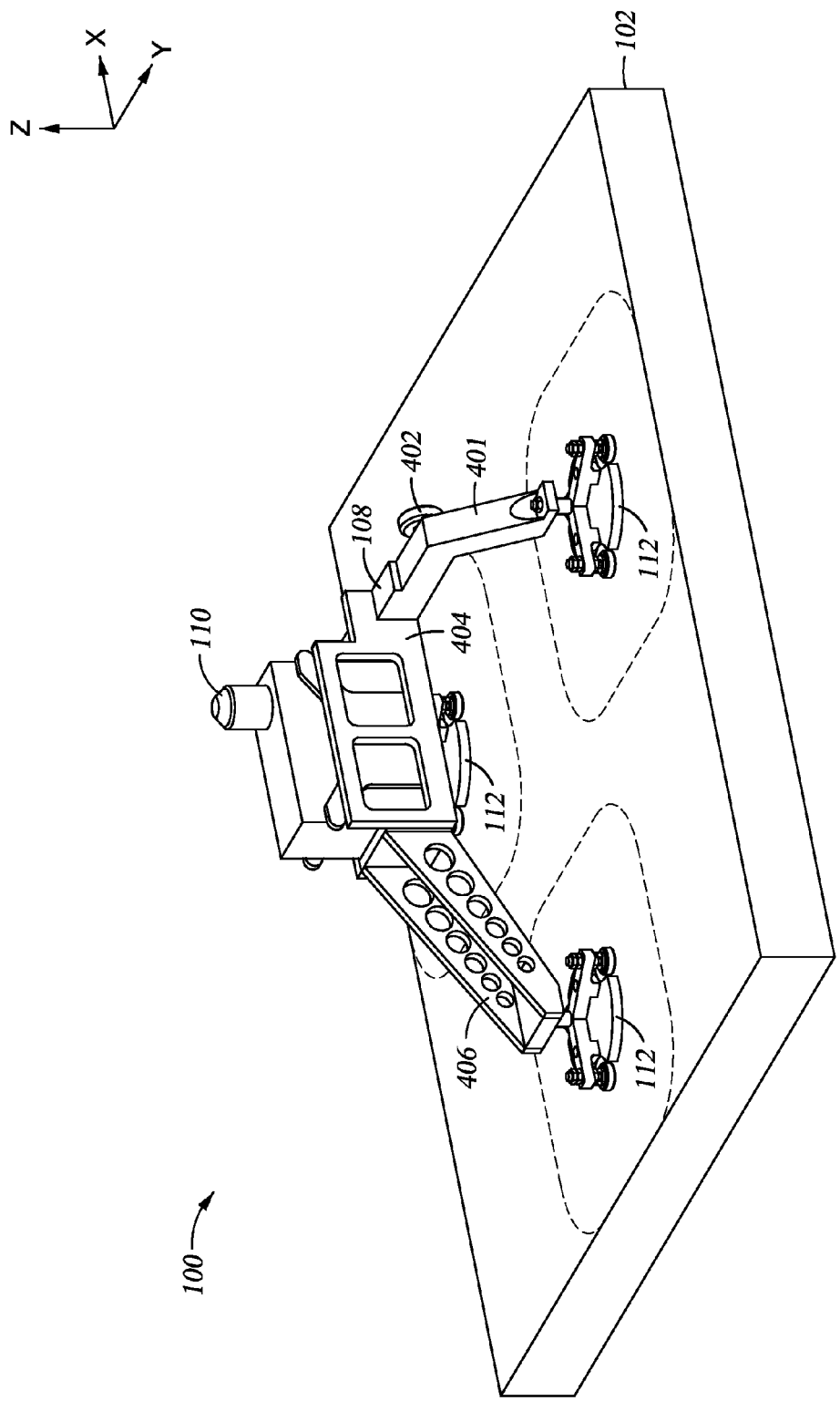
FIGS. 5A-5B illustrate the base and a sensor carrier according to embodiments described herein.
Figure 5B:
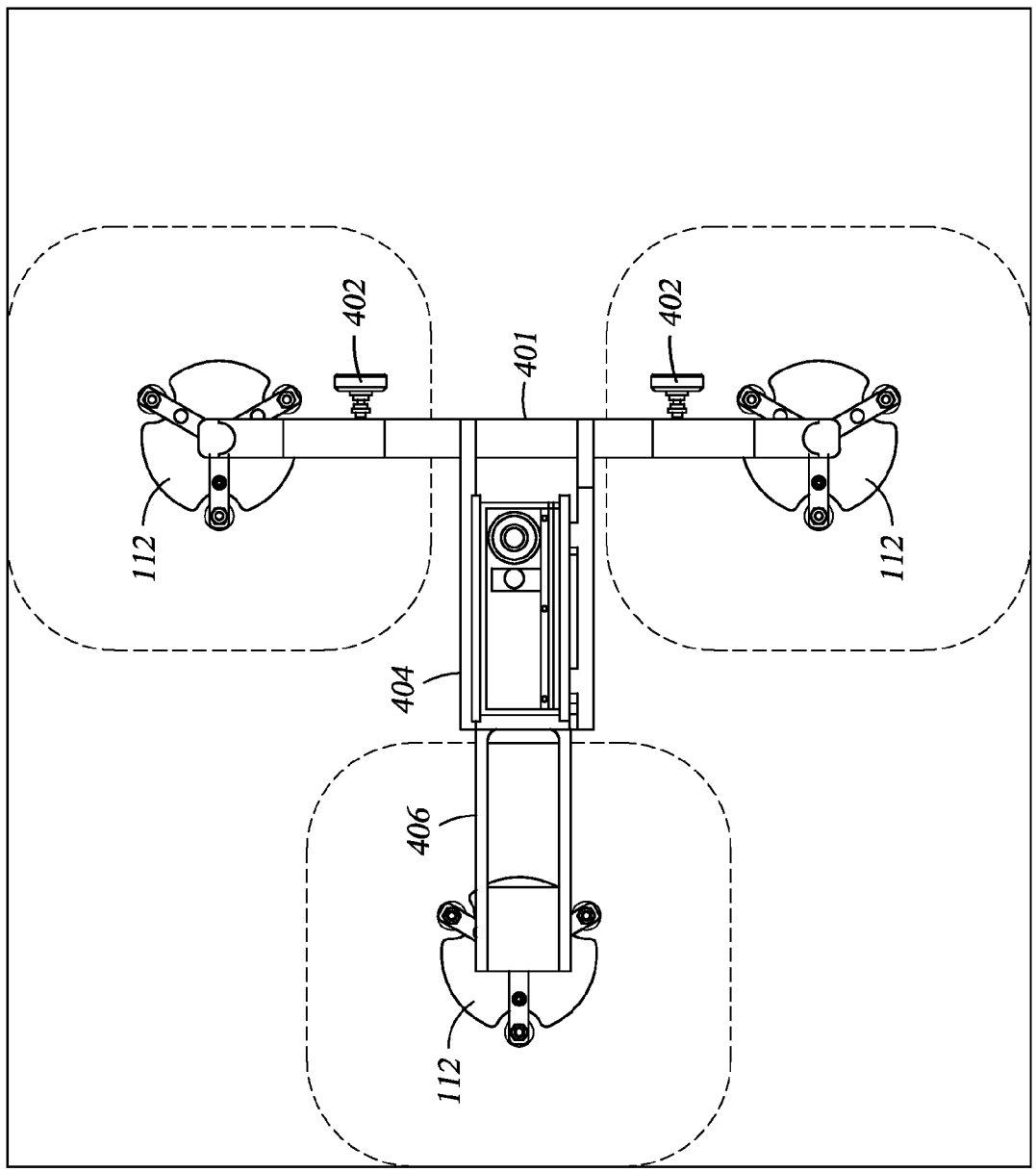

FIGS. 5A-5B illustrate the base 102 and the sensor carrier 108 according to embodiments described herein. FIG. 5A is a perspective view and FIG. 5B is a top view. As shown in FIGS. 5A and 5B, the sensor carrier 108 includes a first beam 401 and one or more air bearings 402 coupled to the first beam 401. A sensor support 404 is coupled to the first beam 401 and the sensor 110 is disposed on the sensor support 404. A second beam 406 is coupled to the sensor support 404. In one embodiment, the second beam 406 may be aligned with the sensor support 404, and both the second beam 406 and the sensor support 404 may extend in a direction that is substantially perpendicular to the first beam 401, as shown in FIG. 5A. In one embodiment, three lifting devices 112 are coupled to the sensor carrier 108, such that two lifting devices 112 are coupled to opposite ends of the first beam 401 and one lifting device 112 is coupled to the end of the second beam 406 opposite the sensor support 404.

FIG. 6 is an enlarged view of a portion of the sensor carrier 108 and the second beam 308 of the second support 106 according to embodiments described herein. As shown in FIG. 6, the bracket 114 has an inner surface 501 facing the sensor carrier 108, and one or more air bearings 502 are coupled to the inner surface 501 of the bracket 114. Each air bearing 502 is aligned with a corresponding air bearing 402 disposed on the sensor carrier 108, and the second beam 308 of the second support 106 is disposed between the air bearings 402, 502. During operation, the lifting device 112 lifts the sensor carrier 108 off the base 102, and the bracket 114 is lifted off the second beam 308 of the second support 106. As the sensor carrier 108 moves in the Y direction by the rotor 306, air coming out of air bearings 402, 502 helps stabilizing the movement of the sensor carrier 108. A flexible material 504 may be disposed on each lifting device 112 to compensate for any uneven area on the base 102. An uneven area on the base 102 may be an area that is not flat, and as a lifting device 112 moving over the uneven area, the lifting device 112 may be in a position that is higher or lower than other lifting devices 112, casing the sensor carrier 108 to tilt. The flexible material 504 helps the lifting device 112 over an uneven area to be on the same level as other lifting devices 112, leading to a more stable movement of the sensor carrier 108.

Figure 7A:
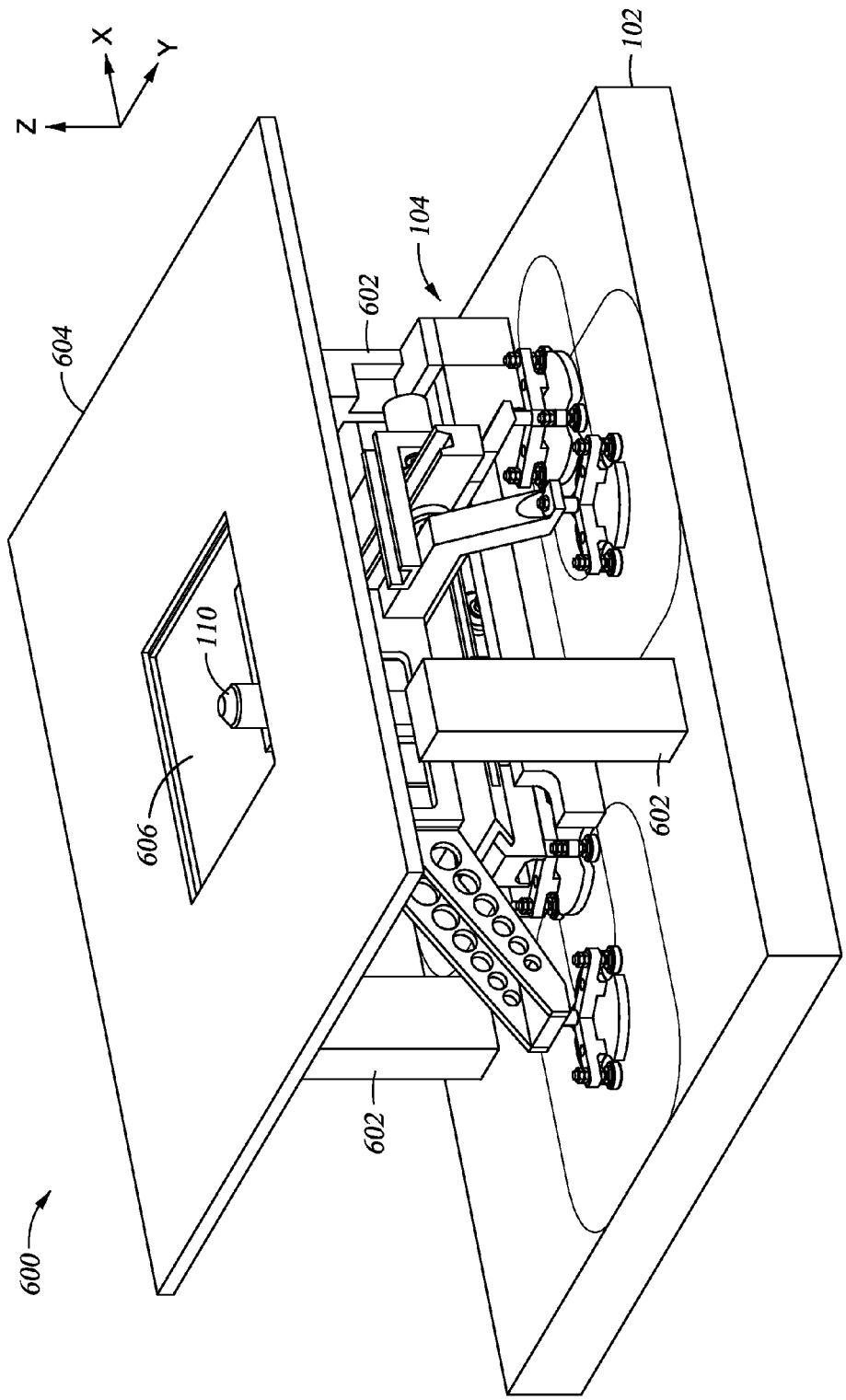
FIGS. 7A-7B illustrate a stage according to embodiment described herein.
Figure 7B:
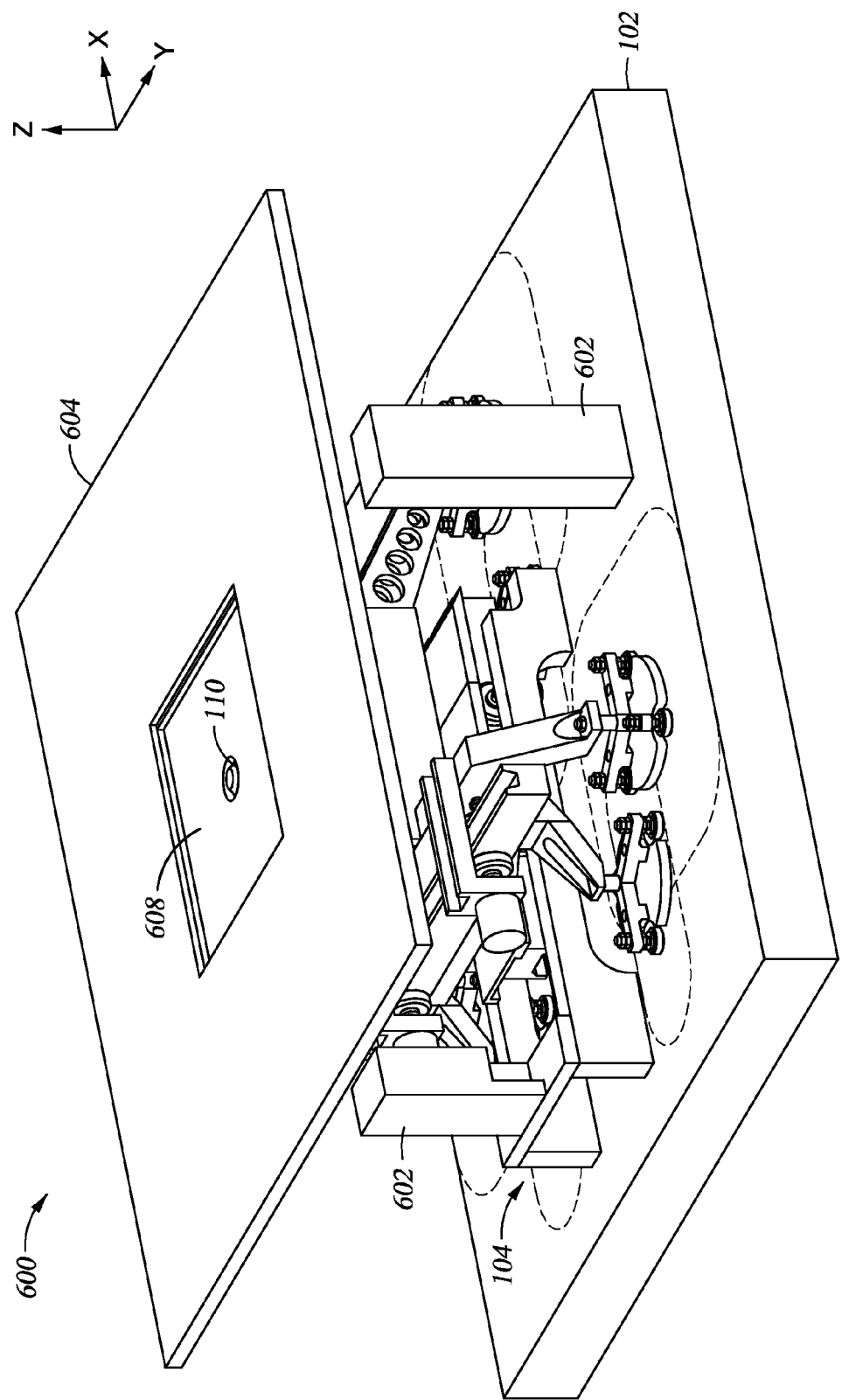

FIGS. 7A-7B are perspective views of a stage 600 according to embodiments described herein. The stage 600 includes the stage 100 shown in FIG. 1, a plurality of vertical supports 602, and a probe card support 604 disposed on the plurality of vertical supports 602. The plurality of vertical supports 602 may be disposed on the first support 104 and on the base 102. In one embodiment, one vertical support 602 is disposed on the first support 104 and two vertical supports 602 are disposed on the base 102. The configuration of the three vertical supports 602 as shown in FIGS. 7A and 7B improves the stability of the probe card support 604 and also enables the probe card support 604 to tilt. The vertical supports 602 are capable of moving the probe card support 604 in the Z direction.

An opening 606 may be formed in the probe card support 604. During operation, a probe card is disposed over the opening 606 on the probe card support 604, and a surface of the probe card containing an array of probes is facing the sensor 110 disposed below. The sensor 110 moves in the X and Y directions to scan the entire surface area of the probe card to determine whether the probe card is ready for testing. FIG. 6B shows a particle plate 608 disposed on the sensor carrier 108. The particle plate 608 is not coupled to the probe card support 604, and the particle plate 608 moves with the sensor carrier 108 during operation. The particle plate 608 is used to prevent particles from falling onto the base 102, interrupting the movement of the sensor carrier 108.

Figure 8:
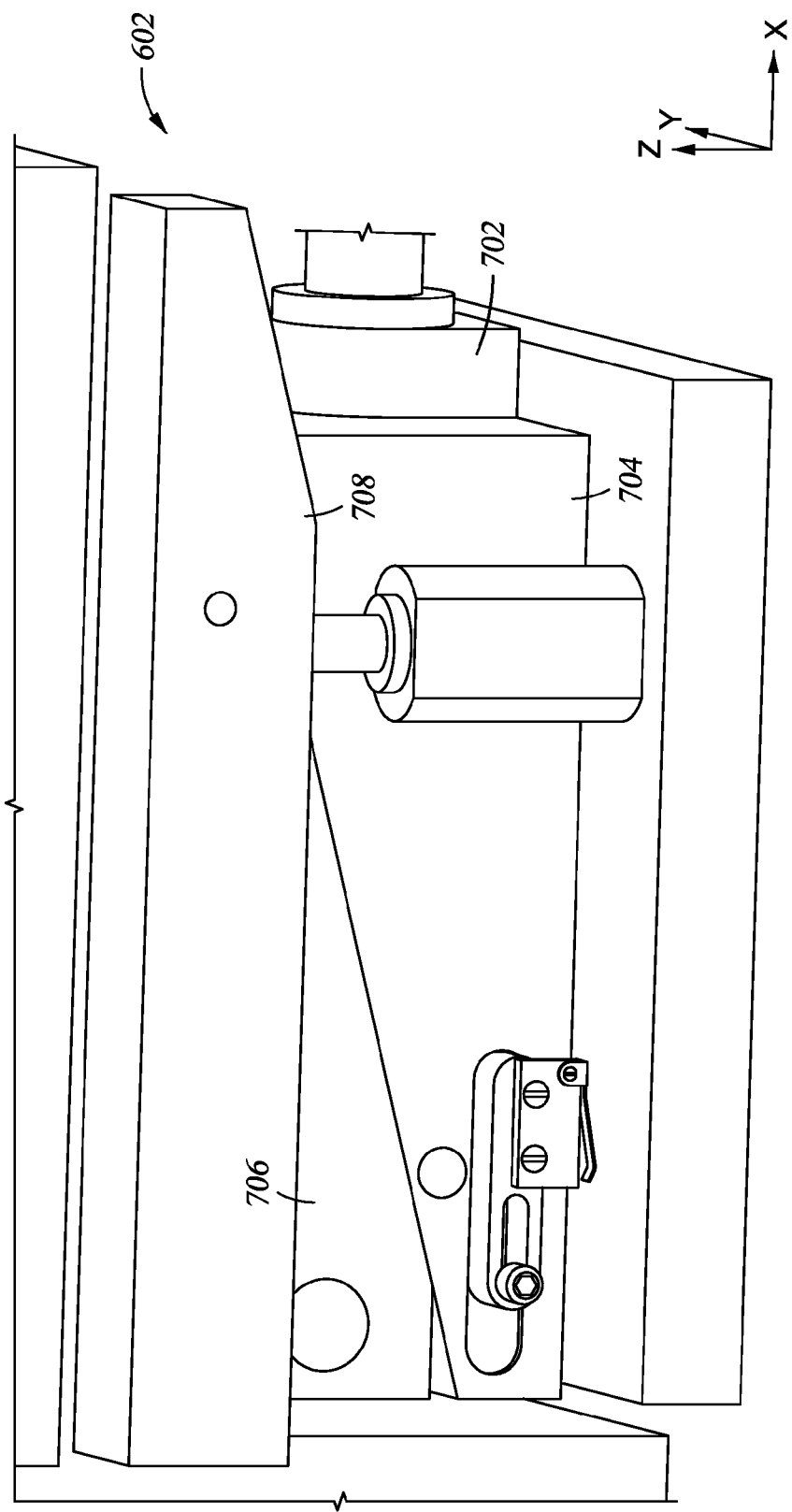
FIG. 8 illustrates a vertical support and tilt adjustment according to embodiment described herein.

FIG. 8 is a side view of the vertical support 602 according to one embodiment described herein. The vertical support 602 includes a motor 702, a first member 704, a second member 706, and a third member 708. The first member 704 and the second member 706 each has a wedge shape, and the second member 706 is disposed on the first member 704. The motor is coupled to the first member 704 and drives the first member 704 to move in a horizontal direction. Because of the wedge shape of the first and second members 704, 706, the horizontal movement of the first member 704 causes the second member 706 to move in a vertical direction (Z direction). The wedge design of the vertical supports 602 provides more precise controlling of the movement of the probe card support 604. In one embodiment, each vertical support 602 can support up to 100 kg. In one embodiment, three vertical supports 602 are utilized to support the probe card support 604, and the vertical supports 602 may have different heights in order to tilt the probe card support 604. The tilting of the probe card support 604 is more controlled due to the vertical supports 602 having more precise control of the vertical movement (in Z direction).

Figure 9:
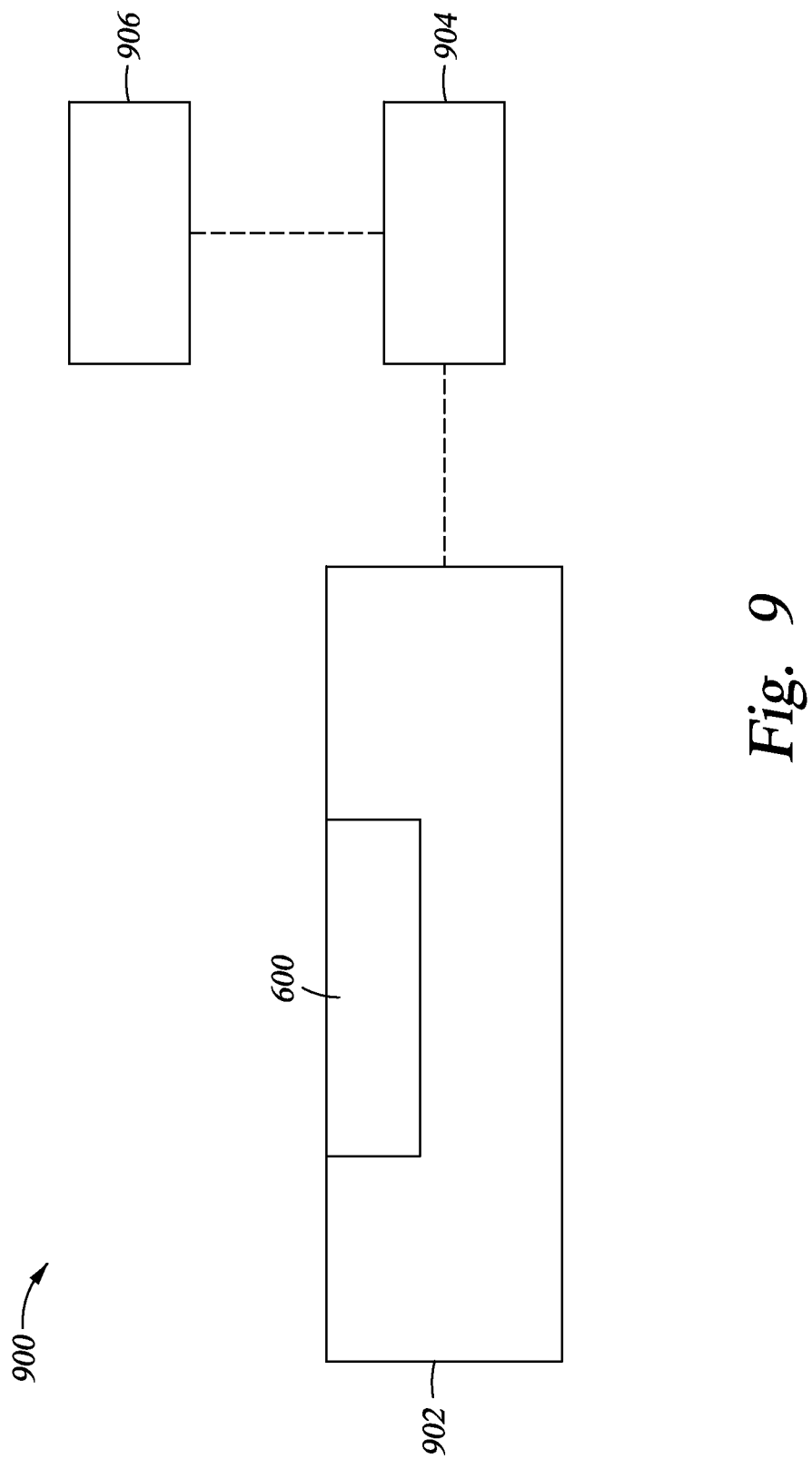
FIG. 9 is schematically illustrates a probe card verification system according to embodiments described herein.

FIG. 9 is a schematic diagram showing a probe card verification system 900 according to embodiments described herein. The probe card and verification system 900 includes an enclosure 902 enclosing the stage 600, a control 904, and a display 906. In one embodiment, the control 904 is a personal computer. The control 904 controls the movement of the sensor and communicates with the sensor to capture images. The control 904 also processes the captured images and determines whether the probe card is ready to be used to test integrated circuit devices.

Figure 10:
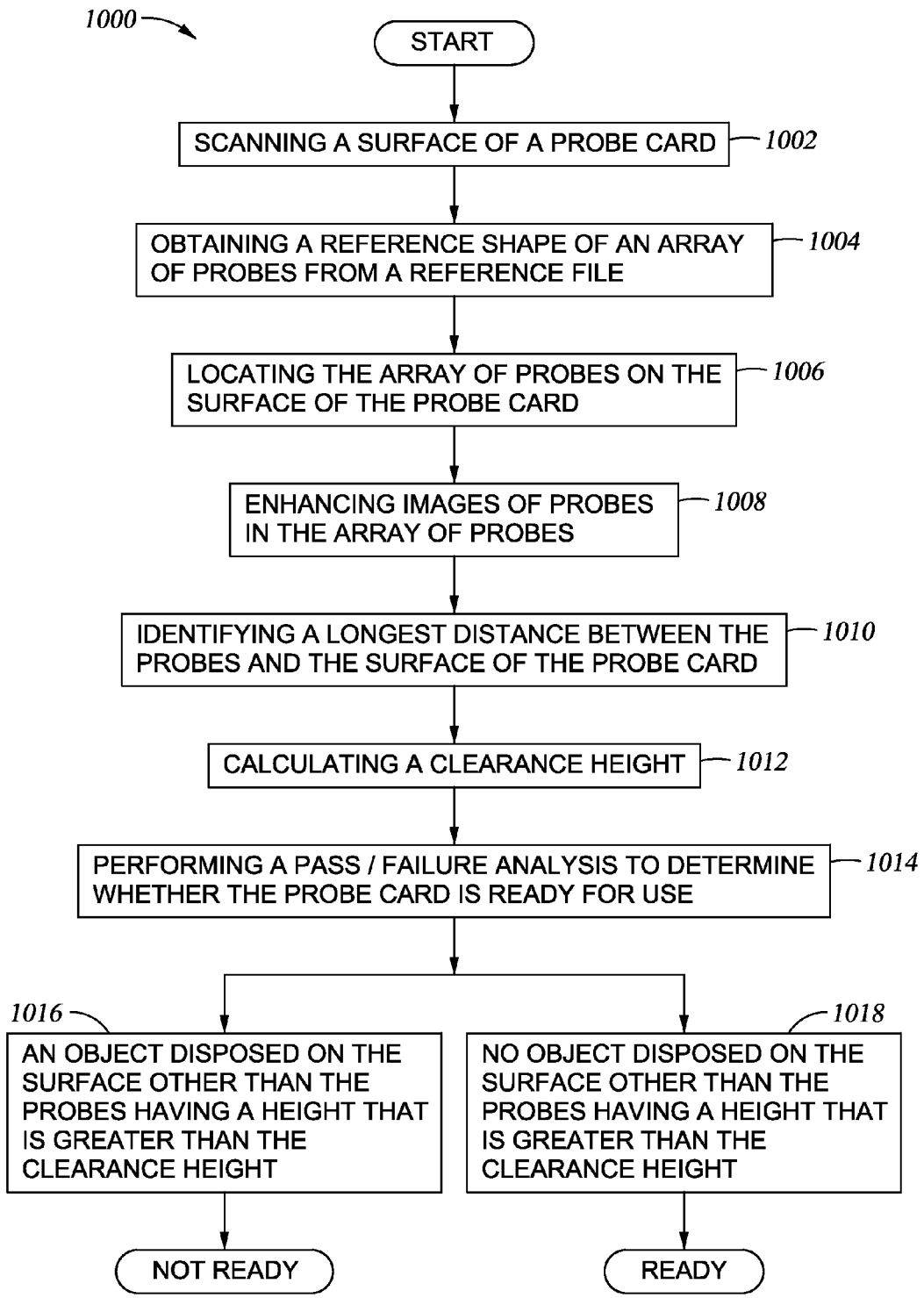
FIG. 10 is a flow chart showing a process to determine whether a probe card is ready for use according to embodiments described herein.

FIG. 10 is a flow chart showing a process 1000 to determine whether a probe card is ready for use according to embodiments described herein. At block 1002, a probe card is placed on a probe card support, such as the probe card support 604 shown in FIG. 7A, and the probe card has a surface facing a sensor disposed therebelow. The sensor may be the sensor 110 shown in FIG. 1. The surface of the probe card is scanned by the sensor, and an image of the surface of the probe card is obtained. The image obtained may show protrusions coming out of the surface, and the protrusions include probes and objects other than the probes, such as screws. The controller, such as the controller 604, cannot make a distinction between the probes and the objects other than the probes. When trying to enhance the image of the probes by running a mathematical filter using the controller, the image of the probes may be erased since the probes are not differentiated from the objects other than the probes.

To resolve this issue, a reference shape of the array of probes is obtained by the controller from a reference file that is stored in or uploaded to the controller, as shown in block 1004. The reference file includes data such as the coordinate of every probe on the surface of the probe card being tested. In one embodiment, the reference shape is a rectangle. At block 1006, the array of probes disposed on the surface of the probe card is located based on the reference shape. If a group of protrusions has the reference shape, the group of protrusions is the array of probes. The actual shape of the array of probes should match with the reference shape. In the event that the actual shape of the array of probes does not match the reference shape due to misalignment of the probe card disposed on the probe card support, the reference shape may be enlarged slightly, allowing the actual shape of the array of probes to fit within the enlarged reference shape, therefore locating the array of probes.

After locating the array of probes on the surface of the probe card, image of the objects such as screws or other particles may be excluded and a mathematical filter may be applied to the image to enhance the image of probes of the array of probes, as shown in block 1008. The enhanced image may help determining whether the probe is damaged. Prior to excluding the objects from the enhanced image, the height of each object is determined and recorded by the controller. The longest distance between the array of probes and the surface of the probe card is also identified, as shown in block 1010. The longest distance between the array of probes and the surface of the probe card may be based on the probe having the longest vertical distance from the surface of the probe card.

When the probe card is in use, the probe card is pressed towards a substrate, and in order to having only the probes to be in contact with the integrated circuit, a minimum vertical distance is required between the probes and other objects. The minimum vertical distance may be stored the reference file as a reference value, and a clearance height is calculated by subtracting the reference value from the longest distance, as shown in block 1012.

Next, a pass/failure analysis is performed to determine whether the probe card is ready for use, as shown in block 1014. If an object disposed on the surface other than the probes having a height that is greater than the clearance height, the probe is not ready, as shown in block 1016. When the probe card is used to test integrated circuits disposed on a substrate, only the probes should be in contact with the integrated circuits. Other objects on the probe card may damage the integrated circuits if the objects are in contact with the integrated circuits. If there are no objects disposed on the surface of the probe card other than the probes having a height that is greater than the clearance height, the probe card is ready for use, as shown in block 1018.

The process 1000 may be performed by a computer program product, and the computer program product may include a computer readable storage medium having computer readable program instructions thereon for causing a processor to carry out the process. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

While the foregoing is directed to embodiments, other and further embodiments may be devised without departing from the basic scope thereof, and the scope thereof is determined by the claims that follow.

The invention claimed is:

1. An apparatus for analyzing a probe card, comprising:
   a stage, wherein the stage comprises:
      a base;
      a first support, wherein the first support comprises two substantially parallel rails that are fixed to the base;
      a second support, wherein the second support is coupled to a first plurality of lifting devices, wherein the second support comprises a first beam disposed between the two rails of the first support, a rotor disposed over the first beam, and a second beam disposed over the rotor;
      a sensor carrier disposed over the first and second supports, wherein the sensor carrier is coupled to a second plurality of lifting devices; and
      a sensor disposed on the sensor carrier.

2. The apparatus of claim 1, further comprising one or more pairs of air bearings disposed on the two rails of the first support, wherein the first beam of the second support is disposed between each pair of air bearings.

3. The apparatus of claim 1, further comprising a bracket coupled to the sensor carrier, and the second beam of the second support is disposed between the bracket and the sensor carrier.

4. The apparatus of claim 3, wherein the sensor carrier includes a first beam, a sensor support, and a second beam.

5. The apparatus of claim 4, further comprising a first one or more air bearings disposed on the first beam and the sensor carrier and a second one or more air bearings disposed on a surface of the bracket facing the sensor carrier and aligned with the first one or more air bearings, wherein the second beam of the second support is disposed between the first and second one or more air bearings.

6. The apparatus of claim 1, wherein the first plurality of lifting devices includes air bearings.

7. An apparatus for analyzing a probe card, comprising:
   an enclosure enclosing a stage, wherein the stage comprises:
      a base;
      a first support, wherein the first support comprises two substantially parallel rails that are fixed to the base;
      a second support, wherein a first plurality of lifting devices is coupled to the second support, wherein the second support comprises a first beam disposed between the two rails of the first support, a rotor disposed over the first beam, and a second beam disposed over the rotor;
      a sensor carrier disposed over the first and second supports, wherein a second plurality of lifting devices is coupled to the sensor carrier; and
      a sensor disposed on the sensor carrier;
   a controller; and
   a display.

8. The apparatus of claim 7, further comprising one or more pairs of air bearings disposed on the two rails of the first support, wherein the first beam of the second support is disposed between each pair of air bearings.

9. The apparatus of claim 7, further comprising a bracket coupled to the sensor carrier, and the second beam of the second support is disposed between the bracket and the sensor carrier.

10. The apparatus of claim 9, wherein the sensor carrier includes a first beam, a sensor support, and a second beam.

11. The apparatus of claim 10, further comprising a first one or more air bearings disposed on the first beam and the sensor carrier and a second one or more air bearings disposed on a surface of the bracket facing the sensor carrier and aligned with the first one or more air bearings, wherein the second beam of the second support is disposed between the first and second one or more air bearings.

* * * * *